US009359602B2

(12) United States Patent
Schrier et al.

(10) Patent No.: US 9,359,602 B2
(45) Date of Patent: *Jun. 7, 2016

(54) IMMUNOSTIMULATORY OLIGODEOXYNUCLEOTIDES

(75) Inventors: Carla Christina Schrier, Boxmeer (NL); Simon Ilg, Nieder-Olm (DE)

(73) Assignee: Intervet Inc., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/119,514

(22) PCT Filed: May 25, 2012

(86) PCT No.: PCT/EP2012/059797
§ 371 (c)(1),
(2), (4) Date: Nov. 22, 2013

(87) PCT Pub. No.: WO2012/160183
PCT Pub. Date: Nov. 29, 2012

(65) Prior Publication Data
US 2014/0199345 A1  Jul. 17, 2014

Related U.S. Application Data

(60) Provisional application No. 61/490,380, filed on May 26, 2011.

(30) Foreign Application Priority Data

May 26, 2011  (EP) .................................... 11167602

(51) Int. Cl.
*C12N 15/11* (2006.01)
*C12Q 1/68* (2006.01)
*A61K 39/39* (2006.01)
*C12N 15/117* (2010.01)
*A61K 39/00* (2006.01)

(52) U.S. Cl.
CPC ................ *C12N 15/11* (2013.01); *A61K 39/39* (2013.01); *C12N 15/117* (2013.01); *C12Q 1/68* (2013.01); *A61K 2039/55561* (2013.01); *C12N 2310/17* (2013.01); *C12N 2310/315* (2013.01); *C12N 2310/341* (2013.01); *C12N 2310/345* (2013.01)

(58) Field of Classification Search
None
See application file for complete search history.

(56) References Cited

U.S. PATENT DOCUMENTS

| 2009/0123467 | A1* | 5/2009 | Bedi et al. .................. 424/134.1 |
| 2009/0253134 | A1 | 10/2009 | Brunner et al. |
| 2010/0003288 | A1* | 1/2010 | Chaung et al. ............. 424/278.1 |
| 2014/0199345 | A1* | 7/2014 | Schrier et al. ............. 424/214.1 |

FOREIGN PATENT DOCUMENTS

| CN | 1810970 A | 8/2006 |
| DE | 10 2006 031 483 A1 | 1/2008 |
| WO | 03/015711 A2 | 2/2003 |
| WO | 2004/058179 A2 | 7/2004 |
| WO | 2006/079291 A1 | 8/2006 |
| WO | 2010/125480 A1 | 11/2010 |

OTHER PUBLICATIONS

Sequence alignment of instant SEQ ID No. 1 with SEQ ID No. 1 in 14119492 filed Nov. 22, 2013.*
Sequence alignment of instant SEQ ID No. 1 with SEQ ID No. 1 in 13976121 filed Jun. 23, 2013.*
Weiner et al. (PNAS. 1997; 94: 10833-10837).*
Domeika et al. (Veterinary Immunology and Immunopathology. 2004; 101: 87-102).*
Kojima et al. (Vaccine. 2002; 20: 2857-2865).*
Brownlie, et al., "Chicken TLR21 acts as a functional homologue to mammalian TLR9 in the recognition of CpG oligodeoxynucleotides", Molecular Immunology, 2009, pp. 3163-3170, vol. 46.
Burger-Kentischer, et al., "A new cell-based innate immune receptor assay for the examination of receptor activity, ligand specificity, signalling pathways and the detection of pyrogens", Journal of Immunological Methods, 2010, pp. 93-103, vol. 358.
Chaung, Hso-Chi, "CpG oligodeoxynucleotides as DNA adjuvants in vertebrates and their applications in immunotherapy", International Immunopharmacology, 2006, pp. 1586-1596, vol. 6.
Dar, et al., "Immunotherapeutic Potential of CpG Oligonucleotides in Chickens", The Journal of Poultry Science, 2009, pp. 69-80, vol. 46.
Iliev, et al., "Immunostimulatory Oligodeoxynucleotide Containing TTTCGTTT Motif from Lactobacillus rhamnosus GG DNA Potentialy Suppresses OVA-specific IgE Production in Mice", Scandinavian Journal of Immunology, 2008, pp. 370-376, vol. 67.
Keestra, et al., "Chicken TLR 21 is an Innate CpG DNA Receptor Distinct from Mammalian TLR9", The Journal of Immunology, 2010. pp. 460-467, vol. 185.
Lee, et al., "Immunostimulatory oligodeoxynucleotide isolated from genome wide screeing of *Mycobacterium bvis* chromosomal DNA", Molecular Immunology, 2006, pp. 2107-2118, vol. 43.
Linghua, et al., "Vaccination with Newcastle disease vaccine and CpG oligodeoxynucleotides induces specific immunity and protection against Newcastle disease virus in SPF chicken", Veterinary Immunology and Immunopathology, 2007, pp. 216-222, vol. 115.
Loots, et al., "CpG motifs as adjuvant in DNA vaccination against Chlamydophila psittaci in turkeys", Vaccine, 2006, pp. 4598-4601, vol. 24.
Pontarollo, et al., "Monocytes are required for optimum in vitro stimulation of bovine peripheral blood mononuclear cells by non-methylated CpG motifs", Veterinary Immunology and Immunopathology, 2002, pp. 43-59, vol. 84.
Rankin et al., "CpG Motif Identification for Veterinary and Laboratory Species Demonstrates That Sequence Recognition is Highly Conserved", Antisense & Nucleic Acid Drug Development, 2001, pp. 333-340, vol. 11.
European Search Report for corresponding EP Application No. EP 11 16 7602, dated Mar. 1, 2012.
PCT International Search Report for corresponding PCT International Search Report for PCT/EP2012/059797, mailed on Aug. 20, 2012.

* cited by examiner

*Primary Examiner* — Shanon A Foley

(57) ABSTRACT

The present invention relates to immunostimulatory oligodeoxynucleotides, vectors and vaccines comprising such oligodeoxynucleotides, to their use as a medicament, to their use in preventing or combating infectious disease, to methods for the detection of such oligodeoxynucleotides and to cells to be used in these methods.

18 Claims, 6 Drawing Sheets

IMMUNOSTIMULATORY OLIGODEOXYNUCLEOTIDES

CROSS-REFERENCE TO RELATED APPLICATIONS

Figure 1:
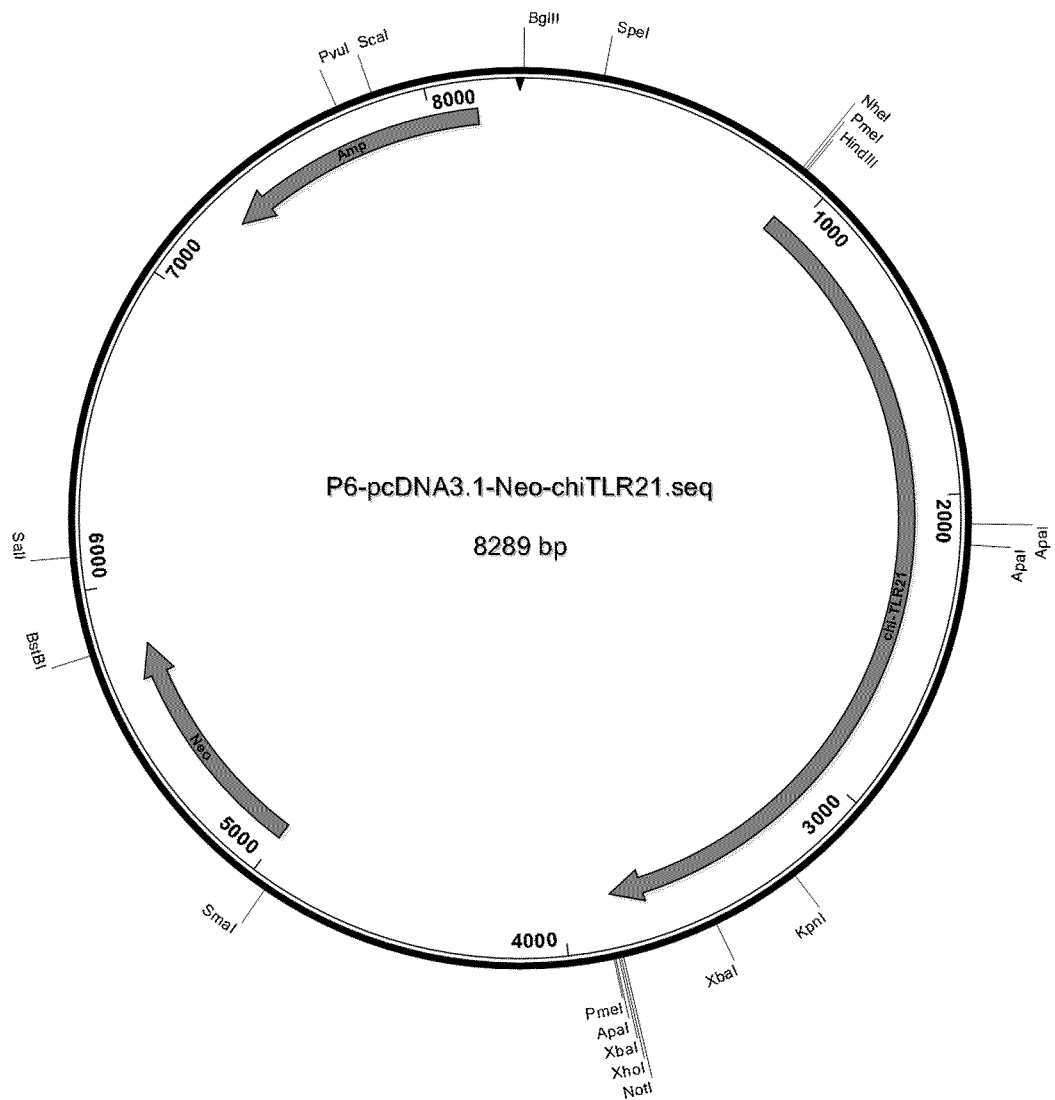
Figure 2:
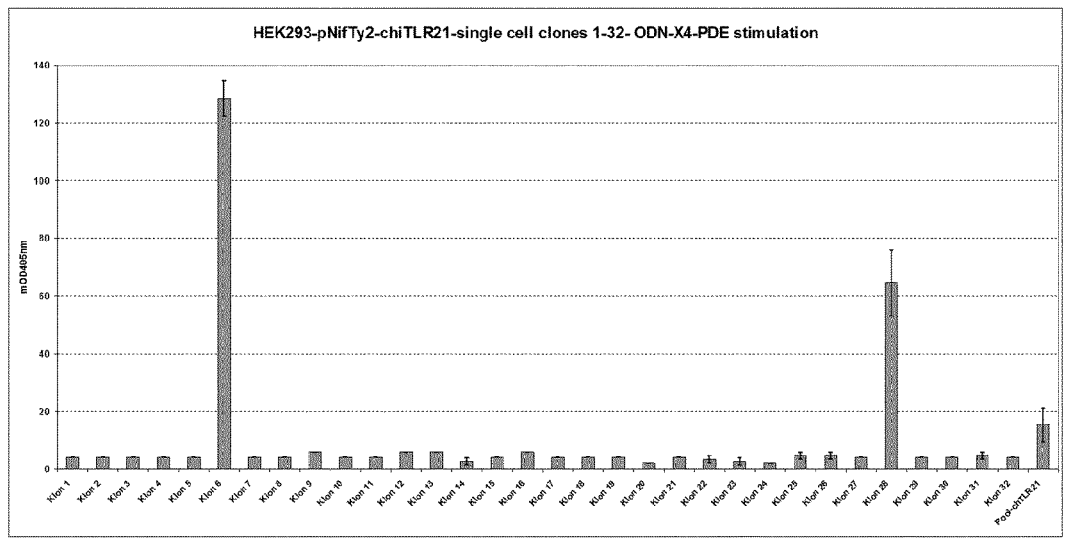
Figure 3:
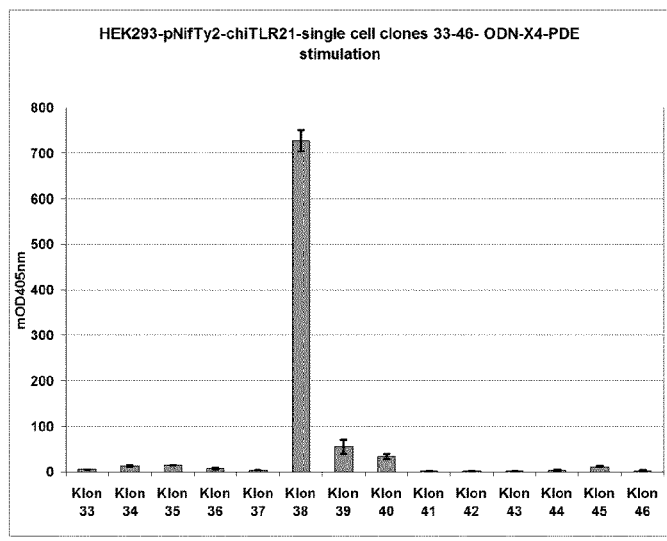
Figure 4:
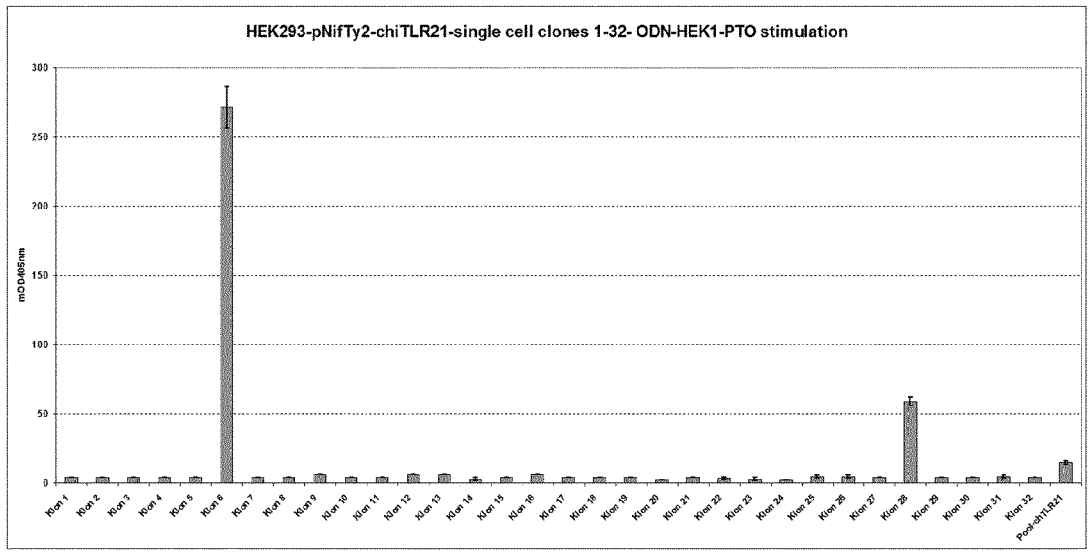
Figure 5:
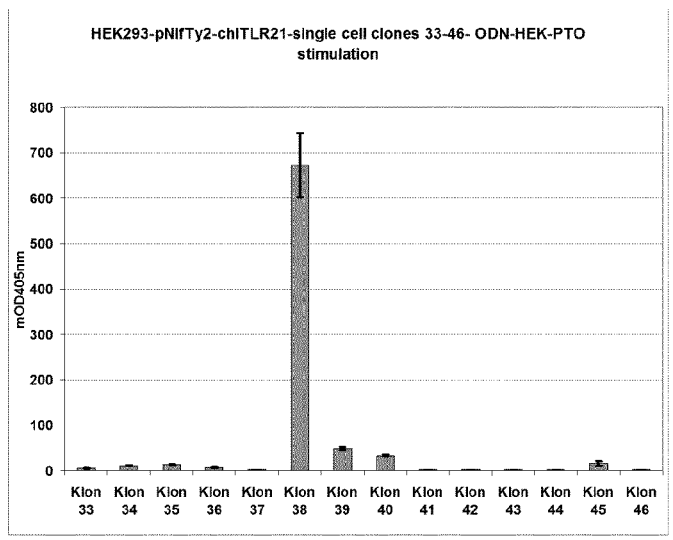

This application is a national stage entry under 35 U.S.C. §371 of PCT/EP2012/059797, filed on May 25, 2012, which claims priority to U.S. Provisional Application No. 61/490, 380 filed on May 26, 2011, and EP Application No. 11167602.9, filed on May 26, 2011. The content of PCT/EP2012/059797 is hereby incorporated by reference in its entirety.

The present invention relates to immunostimulatory oligodeoxynucleotides, vectors and vaccines comprising such oligodeoxynucleotides, to their use as a medicament, to their use in preventing or combating infectious disease, to methods for the detection of such oligodeoxynucleotides and to cells to be used in these methods.

During the past two decades, it has emerged in immunological science that the vertebrate immune system possesses mechanisms to detect microbial infection and to trigger rapid immune activation via the receptor-mediated recognition of unique characteristics of pathogens, the so-called pathogen-associated molecular patterns (PAMPs) interacting with cognate host pathogen recognition receptors (PRRs) (Iwasaki A, Medzhitov R. 2001. *Science* 327, 291-295. Medzhitov R., 2009. *Immunity* 30, 766-775).

It is now clear that certain forms of pathogen deoxyribonucleic acid (DNA) are amongst these PAMPs. In 1995 it was reported that non-methylated CpG motifs in bacterial DNA trigger murine B-cell activation (Krieg et al. 1995). This study generated for the first time a link between the specific recognition of bacterial immunostimulatory non-methylated CpG-containing DNA and the previously recognized CpG suppression as well as the widespread CpG methylation in mammalian DNA. The most effective B cell stimulatory non-methylated CpG oligodeoxynucleotide (CpG ODN) was shown to possess the sequence element GACGTT.

The next landmark paper in the field was published by Shizuo Akira's laboratory in Osaka/Japan (Hemmi et al. 2000). By a gene cloning and a targeted gene knockout approach in mice it could be unequivocally shown, that the cellular response in mice to CpG-ODNs is mediated by the toll-like receptor 9 (TLR9). Subsequently it was shown that the CpG-ODNs are agonists for TLR9 signaling predominantly via the NF kappa-B pathway (Medzhitov 2001). In the following decade, quite a number of studies have been published on basic research topics and on general potential immunotherapeutic applications (e. g. reviewed in Krieg 2002, 2003, 2006; Klinman 2004, Vollmer 2005, Wilson et al. 2006, Kindrachuk et al. 2008, Dorn and Kippenberger 2008, Vollmer and Krieg 2009, Wilson et al. 2009). A number of review articles focus on anti-infective applications of CpG-ODNs (Krieg 2007), the use of TLR9 agonists in the treatment of cancer (Krieg 2007, Weiner 2009), TLR9 activation for asthma and allergy treatment (Kline 2007, Kline and Krieg 2008, Fonseca and Kline 2009) and as vaccine adjuvants (Klinman et al. 2004, Klinman 2006, Daubenberger 2007, Wagner 2009, Mutwiri et al. 2009, Klinman et al. 2009).

CpG ODNs have also been described and discussed as immunostimulatory agents and vaccine adjuvants in veterinary applications, particularly in bovines, pigs, sheep, dogs, chicken and fish (Babiuk et al. 2003, Carrington and Secombes 2006, Griebel et al. 2005, Mutwiri et al. 2003, Singh and O'Hagan 2003, Werling and Jungi 2003).

In the field of veterinary uses in chickens, the use of CpG oligodeoxynucleotides in e.g. vaccines to protect chickens against Newcastle Disease has been described (Linghua 2007).

It has recently been shown that in chicken, TLR21 acts as a functional homologue to mammalian TLR9 in the recognition of CpG oligodeoxynucleotides (Brownlie et al., 2009).

The design of specific CpG ODN's as immunomodulators has so far been quite random. This is especially true for non-mammalian CpG ODN's. The reason for this is multifactorial; first of all there is no knowledge about correlation between immuno modulatory CpG motifs for human TLR's and for TLR's in non-human, let alone non-mammalian species. Secondly, there are no cell-systems available with a sufficiently low background to noise level to selectively test the effects of very low concentrations of CpG ODN's. Moreover, there are no high-throughput screening methods available and even if there were, there is no clear correlation between in vivo versus in vitro efficacy of CpG ODN's as immuno-modulators in non-mammalian species.

Thus, there clearly is a need for novel CpG ODN's that have a high immuno-modulatory effect and therefore are effective in low doses. And there is a need for selective and sensitive CpG ODN selection systems for veterinary purposes that show a correlation between in vitro and in vivo activity of CpG-activity.

It is one of the objectives of the present invention to provide such novel CpG ODN's.

In this respect, one embodiment of the present invention relates to an immunostimulatory non-methylated oligodeoxynucleotide having the general formula $^{5'}[G]_x \{[T]_p \text{ T T C G T C } [T]_q\}_n [G]_z {}^{3'}$ [SEQ ID NO: 25] wherein p=1-15, q=1-15, n=2-100, x=3-10 and z=0-10 or a pharmaceutically acceptable salt thereof.

An "immunostimulatory non-methylated oligodeoxynucleotide" refers to an oligodeoxynucleotide, which contains a non-methylated cytidine-phosphate-guanosine di-nucleotide sequence that stimulates the initiation of signaling cascades leading to activation of transcription factors such as NF-κB or Interferon Regulatory Factor 3 (IRF3). It is this activation that in turn results in the expression of inflammatory cytokines and other cellular activation events. NF-κB binding sites and gene expression influenced by NF-κB are i.a. described by Schindler and Baichwal (1994).

The term oligodeoxynucleotide means a short nucleic acid polymer of deoxynucleotides; i.e. a molecule comprising a multitude of deoxyriboses, linked to a phosphate group and to an exchangeable organic base. Such an organic base is a substituted pyrimidine or a substituted purine. Examples are cytosine and thymine respectively adenine and guanine.

The oligonucleotides according to the invention may comprise modifications. Examples of such modifications are e.g. modifications in the phosphodiester internucleoside bridge located at the 3' and/or 5' end of a nucleoside. Such modifications relate i.a. to the replacement of a phosphodiester by e.g. a phosphorothioate or a phosphorodithioate.

Other modifications are e.g. replacements of a phosphodiester bridge by a dephospho bridge. Examples of dephospho bridges are methylhydroxylamine, formacetal and dimethylenesulfone groups.

Still other modifications are modifications that concern the replacement of a natural nucleoside base by a non-natural nucleoside base such as 5-fluorocytosine, 7-deaza-7-substituted guanine, 7-deaza-8-substituted guanine, 2-thiouracil, dihydrouracil, 5-bromo-cytosine, 6-substituted cytosines, N4-substituted cytosines, Again other modifications are modifications concerning the replacement of a sugar unit; a β-ribose sugar or a β-D-2'-ribose sugar unit by a modified sugar unit such as e.g. an L-2'-deoxyribose or 2'-L-arabinose.

A text book giving further insight in oligonucleotides is e.g. "PCR Primer: A Laboratory Manual", Second Edition, 2003, Edited By Carl W. Dieffenbach, *National Institute of Allergy and Infectious Diseases*; Gabriela S. Dreksler, *Uniformed Services University of the Health Sciences*, Cold Spring Harbor Laboratory Press ISBN 978-087969654-2.

The structure $\{[T]_p\ T\ T\ C\ G\ T\ C\ [T]_q\}_n$ [SEQ ID NO: 26] carrying the CpG motif represents the active immunostimulating moiety of an ODN according to the invention. Therefore, the present invention provides immunostimulatory oligodeoxynucleotides that comprise this so-called "backbone".

It was found that the backbone of an oligodeoxynucleotide according to the invention, the structure $\{[T]_p\ T\ T\ C\ G\ T\ C\ [T]_q\}_n$ [SEQ ID NO: 26] must be present at least two, preferably three times. Therefore, n should be at least two. It was also found that the activity of the oligodeoxynucleotides increases when n increases. This effect is leveling when n increases. Basically, the number n of the backbone structure should therefore be at least 2. Preferably, the range of n is $3 \leq n \leq 100$, merely because of the fact that the longer the synthetic sequence the more difficult it is to make. In practice preferably the range of n is $2 \leq n \leq 18$. More preferably, the range of n is $3 \leq n \leq 18$, even more preferably the range of n is $4 \leq n \leq 18$, still even more preferably the range of n is $5 \leq n \leq 18$.

The identification of CpG ODN's according to the invention was made possible i.a. by using a more selective detection system than the systems currently in use for the detection of NF-κB activation. Brownlie at al. (2009) describe an NF-κB luciferase based reporter system. Other systems are e.g. based upon IL-8 transcript measurement or cytokine secretion or the detection of NO secretion.

Contrary to this, in the present invention a secreted alkaline phosphatase based detection system (SEAP) was used. SEAP is a reporter enzyme in mammalian systems (Yang et al., 1997). This system turned out to be surprisingly sensitive and in addition surprisingly provides a close correlation between the in vitro and in vivo activities of the CpG ODN's tested. The SEAP system was used with para-nitrophenylphosphate (pNPP) as a substrate.

Another improvement over existing systems was the introduction and stable maintenance in cells of the plasmid carrying the SEAP gene. Up till now, all detection systems used transient transfection of cells with the reporter gene. It is due to the introduction and stable maintenance in cells of the reporter gene that now for the first time a dose/response curve could be made. Such a curve is essential if a reliable comparison between various CpG ODN's activity is to be made.

Therefore, the methods and cell lines described in detail in the Examples section of the present invention allow for the first time to make a reliable side-by-side comparison between various CpG ODN's.

Further details of the system used are given in the Examples section.

Since the present methods and cell lines now allow such reliable side-by-side comparisons between various CpG ODN's, it could be determined that an oligodeoxynucleotide according to the invention wherein p>1 has a higher activity level than when p=1. Therefore, in a preferred form of this embodiment, p>1. A p-value of 2, 3, 4, 5, or 6 are more preferred in that order of preference. Still more preferred are p-values of >6, although the increase in activity levels off.

P-values that exceed 15 would be increasingly difficult to synthesize. Therefore, preferably, the value for p should not exceed 15.

It could also be determined that an oligodeoxynucleotide according to the invention wherein q>1 has a higher activity level than when q=1. Therefore, in a preferred form of this embodiment, q>1. A q-value of 2, 3, 4, 5, or 6 are more preferred in that order of preference. Still more preferred are q-values of >6, although the increase in activity levels off.

Q-values that exceed 15 would be increasingly difficult to synthesize. Therefore, preferably, the value for q should not exceed 15.

It was found that an increase in the number of G's at the 5'-end of the structure $^{5'}[G]_x\ \{[T]_p\ T\ T\ C\ G\ T\ C\ [T]_q\}_n\ [G]_x\ ^{3'}$ [SEQ ID NO: 25] leads to an increase of the activity of the CpG ODN. The value x should be at least 3, but increasing numbers of G's up to 20 G's improve the activity of the CpG ODN. Therefore preferably, x is 4, 5, 6, 7, 8, 9, 10, 11, 12, 13, 14, 15, 16, 17, 18, 19 or 20 in that increasing order of preference.

It was also found that an increase in the number of G's at the 3'-end of the structure $^{5'}[G]_x\ \{[T]_p\ T\ T\ C\ G\ T\ C\ [T]_q\}_n\ [G]_z\ ^{3'}$ [SEQ ID NO: 25] leads to a (slight) decrease of the activity of the CpG ODN. The value z should be 10 or less than 10, but decreasing the number of G's down to 0 G's improves the activity of the CpG ODN. Therefore more preferably z is 9, 8, 7, 6, 5, 4, 3, 2, 1 or 0, in that increasing order of preference.

As said above, several kinds of modifications in the phosphodiester internucleoside bridge located at the 3' and/or 5' end of a nucleoside are feasible. But basically, depending upon the way of synthesis, usual common types of bonds between two nucleotides are: phosphodiester (PDE) bonds and phosphorothioate (PTO) bonds. In order to improve the stability and the immunostimulatory effect of CpG ODN's, the building blocks of synthetic oligodeoxynucleotides are provided with phosphorothioates, so that they form PTO bond. It was surprisingly found, however, that when only the $^{5'}[G]_x$ and the $^{3'}[G]_z$ nucleotides are bound by PTO bonds and the other nucleotides are bound by PDE bonds, the efficacy of the oligodeoxynucleotide according to the invention is further increased. (In such cases, the $^{5'}[G]_x$ to $\{[T]_p\ T\ T\ C\ G\ T\ C\ [T]_q\}$ [SEQ ID NO: 26] bond is a PTO bond, while the $\{[T]_p\ T\ T\ C\ G\ T\ C\ [T]_q\}$ to $[G]_z\ ^{3'\ [SEQ\ ID\ NO:\ 26]}$ bond is a PDE bond.)

Therefore, another preferred form of this embodiment relates to oligodeoxynucleotides according to the invention wherein the $^{5'}[G]_x$ and the $^{3'}[G]_z$ nucleotides have a phosphorothioate binding and the other nucleotides have a phosphodiester binding.

It is not necessary that the backbone of oligodeoxynucleotides according to the invention, the structure $^{5'}\{[T]_p\ T\ T\ C\ G\ T\ C\ [T]_q\},\ ^{3'}$ [SEQ ID NO: 26] is identical for every n. This means that an oligodeoxynucleotide backbone according to the invention could look i.a. like this: {T T T C G T C T} {T T T C G T C T T} {T T T T C G T C T} [SEQ ID NO: 22]. Such a series of three different consecutive different backbones would be indicated as a heteropolymer. A stretch of three identical copies would be called a homopolymer. Preferably, the oligodeoxynucleotide according to the invention comprises a $^{5'}\{[T]_p\ T\ T\ C\ G\ T\ C\ [T]_q\}_n\ ^{3'}$ [SEQ ID NO: 26] homopolymer.

The CpG oligodeoxynucleotides according to the invention are active in picomolar (sub-nanomolar) amounts; their EC50 is below 1 nM.

The half-maximal effective concentration (EC50) of an oligodeoxynucleotide is the amount of oligodeoxynucleotide that is necessary to induce an amount of the reporter enzyme SEAP (that produces the colored product absorbing at 405 nm) in the reporter cells (HEK293-pNifty2-chickenTLR21 or HD11-pNifTy2Hyg) that gives a half-maximal enzymatic reaction rate. If the EC50 of an oligodeoxynucleotide is below 1 nM in these cells, it is considered to be active in picomolar (sub-nanomolar) amounts.

It is very well possible to link an oligodeoxynucleotide according to the invention to a carrier or hapten, via a reactive chemical group. Such linkage enhances the immunostimulatory effect of the combined molecules.

Mere examples of such components are e.g. digoxigenin, aminohexyl-, Texas red and biotin. Preferred carriers or haptens are 3'- and 5'-labeled Texas red and 5'-labeled digoxigenin. The linkage of oligodeoxynucleotides to haptens/carriers is well-known in the art.

Another embodiment of the invention relates to a vector comprising an immunostimulatory non-methylated oligodeoxynucleotide according to the invention. Such a vector can be a nucleic acid molecule such as a plasmid, a virus, a bacteriophage or any other vector used in molecular biology. Merely as an example: a vector comprising an immunostimulatory non-methylated oligodeoxynucleotide can e.g. be a DNA molecule such as a plasmid that can be multiplied in bacteria, into which an immunostimulatory non-methylated oligodeoxynucleotide according to the invention has been cloned. Such a plasmid preferably has an active origin of replication, causing high numbers of the plasmid to be present in the host. Growing such bacteria on a large scale followed by isolation of the plasmids provides an alternative for the synthetic production of the immunostimulatory non-methylated oligodeoxynucleotide according to the invention.

One of the aims of the present invention is to provide new CpG ODN's that can be used as successful immunostimulating components in vaccines that prevent or combat infectious disease together with an antigen component or genetic information encoding an antigen component, and a pharmaceutically acceptable carrier.

In general, the term antigen component refers to a composition of matter that comprises at least one epitope that can induce, stimulate or enhance an immune response when administered to a human or an animal.

The antigen component may be any kind of antigen component but preferably is derived from a micro-organism or virus that in its wild-type form is pathogenic to humans or animals.

The antigen component can be the whole pathogen, preferably in an inactivated or attenuated form, an extract of the pathogen or an immunogenic protein of the pathogen.

If the antigen component is an immunogenic protein of the pathogen, that immunogenic protein is preferably expressed in and recovered from in vitro cultured cells.

Therefore, another embodiment relates to a vaccine for preventing or combating infectious disease characterised in that said vaccine comprises an immunostimulating amount of an oligodeoxynucleotide according to the invention and/or a vector according to the invention, an immunogenic amount of an antigen component or genetic information encoding an antigen component, and a pharmaceutically acceptable carrier.

Of course, the immunostimulating amount of the oligodeoxynucleotide and the immunogenic amount of the antigen component are strongly interrelated. It is one of the merits of the present invention that the presence of the oligodeoxynucleotide according to the invention can lower the amount of antigen component that is necessary to prevent or combat infectious disease.

The amount of antigen component that is necessary to prevent or combat infectious disease is referred to as the immunogenic amount of the antigen component.

An immunostimulating amount of the oligodeoxynucleotide is the amount that is capable of decreasing the immunogenic amount of the antigen component, i.e. the amount of the antigen component that is necessary to prevent or combat an infectious disease.

So basically, the wording "immunostimulating amount of the oligodeoxynucleotide" and "immunogenic amount" must be seen in relation to each other.

It goes without saying that, if the vaccine comprises genetic information encoding an antigen component, the amount of antigen component expressed by this genetic information should be enough to prevent or combat infectious disease, i.e.; it must be an immunogenic amount.

The fact that the non-methylated oligodeoxynucleotides according to the invention are immunostimulatory, means that they enhance the immunological efficacy of antigen components in vaccines. For that reason, vaccines according to the invention will in many cases comprise less of the antigen component or the genetic information encoding the antigen component than would be the case if no oligodeoxynucleotides according to the invention would be present.

In some cases an antigen component as such, without the addition of immunostimulatory oligonucleotides, may have such low immunogenic properties that high amounts must be given anyway, albeit without reaching the desired immunogenic level. In such cases, the antigen component can be given in the usual high concentration, however now together with an oligodeoxynucleotide according to the invention in order to so obtain the desired level of immunogenicity.

Thus, the amount of the antigen component or the genetic information encoding the antigen component to be administered with a oligonucleotide according to the invention would as a rule of thumb be equal or below the amount given in the absence of the oligonucleotide. The skilled person involved in the manufacturing of a specific vaccines, would know that amount for that specific vaccine. Also, the Examples give e.g. ample guidance for the amount of antigen components to be used, e.g. in three different inactivated viral vaccines: Newcastle disease virus vaccine, Infectious Bronchitis virus vaccine and Turkey Rhinotracheitis vaccine.

The amount of the oligodeoxynucleotide according to the invention that needs to be administered together with the antigen component or the genetic information encoding the antigen component depends both on the selected oligodeoxynucleotide and the antigen component.

A very suitable amount of oligodeoxynucleotide according to the invention would usually vary between 1 and 100 nanomol. Very good in vivo results have e.g. been obtained with 1-10 µg of oligodeoxynucleotides according to the invention with an average length of 30 deoxynucleotides that were shown to be active in in vitro tests in the nanomolar range.

If an oligodeoxynucleotide is chosen from the group of oligodeoxynucleotides that are active in the picomolar range, the skilled person would realise that amounts below, possibly far below, 1 nanomol, i.e. picomolar amounts, would be worth testing before testing nanomolar amounts.

Vaccines according to the invention comprise a pharmaceutically acceptable carrier. The nature of this carrier depends i.a. upon the route of administration. If the administration route is through the oral or intranasal route, the carrier could be as simple as sterile water, a physiological salt solution or a buffer. If injection is the preferred route, the carrier should preferably be isotonic and have pH restrictions that make it suitable for injection. Such carriers however are extensively known in the art.

Vaccines according to the invention may, in addition to the antigen component or the genetic information encoding the antigen component, and an oligodeoxynucleotide according to the invention, comprise an adjuvant. Adjuvants in general are substances that boost the immune response of the host in a non-specific manner.

Many adjuvants are known in the art to be suitable, such as Freund's Complete and Incomplete adjuvant, vitamin E, non-ionic block polymers and polyanions such as dextran sulphate, carbopol and pyran, alum hydroxide. Also frequently used are alum phosphate, saponins, vegetable oils such as tocopherol and mineral oils. Very efficient adjuvants are oil-in-water emulsions and especially water-in-oil emulsions, further also referred to as are oil-in-water adjuvants and water-in-oil adjuvants. Such emulsions are well-known in the art. Thus, preferably, the vaccine comprises a water-in-oil adjuvant.

Preferably the antigen component is, or is derived from a virus or micro-organism that in its wild-type form is pathogenic to poultry.

More preferably, said virus or micro-organism is selected from the group consisting of Infectious Bronchitis virus, Newcastle Disease virus, Infectious Bursal Disease (Gumboro), Chicken Anaemia agent, Avian Reovirus, *Mycoplasma gallisepticum*, Turkey Rhinotracheitis virus, *Haemophilus paragallinarum* (Coryza), Chicken Poxvirus, Avian Encephalomyelitis virus, Egg Drop syndrome virus, Infectious Laryngotracheitis virus, Herpes Virus of Turkeys, Eimeria species, *Ornithobacterium rhinotracheale*, *Pasteurella multocida*, *Mycoplasma synoviae*, *Salmonella* species and *Escherichia coli*.

Again another embodiment of the present invention relates to an immunostimulatory non-methylated oligodeoxynucleotide according to the invention for use as a medicament Again another embodiment of the present invention relates to an immunostimulatory non-methylated oligodeoxynucleotide according to the invention for use in preventing or combating infectious disease in poultry Up till now, all detection systems used transient transfection of cells with the reporter gene. Such transient systems do not allow for a reliable side-by-side comparison of the efficacy of CpG ODN's. As said above, a major improvement over existing systems was the introduction and stable maintenance in cells, of the plasmid carrying the reporter gene. Stable means that the plasmid remains present in the cell after several cell division cycles.

Frequently, stable maintenance of a plasmid is obtained by growing the cells under the pressure of one or more selective agents, such as antibiotics for which a resistance gene is present on the plasmid. Loss of the plasmid would then cause the cell that lost the plasmid to die. Remaining viable cells would still harbour the plasmid.

Another way of stable maintenance would be transfection with linearized plasmids. Such plasmids usually become integrated in the genome of the cell, and thus be stably maintained. Thus, still another embodiment of the present invention relates to a cell comprising a TLR21-receptor and a plasmid encoding an NF-κB reporter gene, which plasmid is stably maintained in the cell. Such cells are very suitable for use in the screening of CpG molecules, more specifically the screening of CpG molecules according to the invention.

The Examples give ample guidance about how to obtain such a cell comprising a plasmid encoding a reporter gene that can be stably maintained in the cell.

As also mentioned above, detection systems based upon secreted alkaline phosphatase (SEAP) were shown to be very suitable for the detection system used.

Thus, preferably the reporter gene is a gene encoding secreted alkaline phosphatase.

Basically, any cell or cell line carrying and expressing a TLR21 that allows introduction and preferably the stable maintenance of a plasmid carrying a NF-κB reporter gene, preferably the SEAP gene as described above is suitable for testing TLR21-specific CpG ODN's.

A preferred example of such a suitable cell line for testing TLR21-specific CpG ODN's is the chicken cell line HD11.

Therefore, preferably, a cell line for use in the detection system is a HD11 cell line comprising a stable plasmid encoding a reporter gene.

Chicken cell lines such as the HD11 cell line display a whole panel of chicken-TLR's. This may in certain conditions generate a certain background activity.

Therefore, non-poultry cell lines such as mammalian cell lines are more preferred cell lines. An example of such a mammalian cell line is a HEK293 cell into which the TLR21 has been cloned. Such a cell line is more specifically selective for TLR21-activating signals.

Therefore, more preferably, a cell line for use in the detection system is the mammalian cell line HEK293 comprising a stably maintained reporter gene and into which HEK293 cell the TLR21 has been cloned.

Still another embodiment of the present invention relates to a method for the detection of immunostimulatory oligodeoxynucleotides according to the invention wherein that method comprises the steps of a) contacting an oligodeoxynucleotide with a cell according to the invention, b) detecting the level of product of the reporter gene.

In a preferred form of this method, the product of the reporter gene is SEAP

A more preferred form of this embodiment relates to a method for the detection of immunostimulatory oligodeoxynucleotides according to the invention, wherein the cell is a cell of chicken cell line HD11, or a HEK293 cell line into which chicken TLR21 has been cloned.

EXAMPLES

Example 1

Gene Cloning and Heterologous Expression of Chicken TLR21

Recent progress in chicken TLR research suggests that TLR21 is the functional homolog of mammalian TLR9 in avian species (Keestra 2008, Brownlie et al. 2009).

Outline of TLR21 Gene Cloning

Based on the Genbank database sequence NM_001030558, a primer pair was synthesized for the polymerase chain reaction (PCR) amplification of the chicken TLR21 gene:

```
Ga-TLR21-for1                      [SEQ ID NO: 1]
GAAGCTTACCATGATGGAGACAGCGGAGAAGGC Ga-TLR21-rev1                      [SEQ ID NO: 2]
GGCGGCCGCTACATCTGTTTGTCTCCTTCCCTG
```

The primers were designed to provide flanking restriction cloning sites (underlined) and a Kozak sequence (italic) to the start and stop codons (bold). RT-PCR was performed using these primers and chicken spleen total RNA as a template. A PCR product of the expected size (~3000 bp) was cloned into pCR2.1-Topo and 5 independent plasmid clones (P1, P2, P12, P13, P14) were sequenced.

DNA sequence of chicken TLR21, as used.
[SEQ ID NO: 3]

AAGCTTACCATGATGGAGACAGCGGAGAAGGCATGGCCCAGCACCAGGAT
GTGCCCCTCCCACTGCTGTCCACTCTGGCTGCTGCTGCTGGTGACAGTGA
CACTGATGCCGATGGTGCACCCGTATGGCTTTCGCAACTGCATTGAGGAT
GTCAAGGCACCTTTGTACTTCCGCTGCATCCAGCGCTTCCTGCAGTCGCC
GGCCCTGGCAGTGTCTGACCTGCCACCACATGCCATCGCGCTCAATCTGT
CATACAACAAAATGCGCTGCCTGCAGCCCTCTGCCTTTGCCCACCTGACA
CAGCTGCATACCCTGGACCTGACCTACAACCTCCTGGAGACCCTCTCCCC
TGGTGCCTTCAATGGGCTGGGTGTGCTGGTGGTGCTGGACCTGTCTCACA
ACAAGCTGACCACACTTGCTGAAGGGGTGTTCAACAGCTTGGGCAACCTG
TCCTCGCTGCAGGTACAACATAACCCCCTCAGCACGGTGTCACCAAGTGC
TCTGCTACCCCTGGTCAACCTGCGCCGCCTGTCTCTACGGGCGGGCGGC
TGAATGGGTTGGGGGCAGTGGCAGTGGCAGTGCAGGGCTTGGCACAGCTG
GAGCTGTTGGACCTATGTGAAAACAACCTGACAACGCTGGGGCCAGGCCC
ACCGCTACCCGCCTCGCTGCTCACCCTGCAGCTGTGCAACAACTCGCTGA
GGGAGTTAGCGGGGGGCAGCCCGGAGATGCTATGGCACGTGAAGATACTC
GACCTCTCCTACAACAGTATCTCACAGGCGGAGGTCTTCACCCAGCTCCA
CCTGCGCAACATCAGCCTGCTCCACCTGATCGGCAACCCCTTGGATGTCT
TCCACCTGTTGGACATCTCTGACATCCAACCTCGCAGCCTGGATTTCTCT
GGGTTGGTGCTGGGGGCTCAGGGGCTGGATAAGGTGTGCCTGAGGCTGCA
GGGTCCCCAGGCCTTGCGGCGGCTGCAGCTACAACGCAACGGGCTGAAGG
TGCTGCATTGTAATGCACTGCAGTTGTGTCCTGTGCTGAGAGAGCTGGAC
CTGTCCTGGAACCGGCTACAGCACGTGGGCTGTGCCGGCCGGCTGCTGGG
CAAGAAGCAGCGGGAGAAGCTGGAAGTGCTGACAGTGGAACACAACCTGC
TGAAGAAACTGCCGTCTTGCCTGGGGGCCCAGGTGCTGCCTCGGCTGTAC
AACATTTCCTTCCGCTTTAACCGCATCCTGACTGTTGGGCCCCAAGCCTT
TGCCTACGCCCCGGCCCTGCAGGTGTTGTGGCTCAATATTAACAGCCTGG
TGTGGCTGGACAGGCAGGCACTGTGGAGGCTGCACAACCTGACAGAGCTG
CGCCTGGACAACAACCTGCTGACCGACCTCTATCACAACTCCTTCATTGA
CCTCCACAGACTGCGCACCCTCAACCTGCGCAACAACCGTGTCTCCGTCC
TCTTCTCTGGTGTCTTCCAGGGGCTGGCTGAGCTGCAGACGCTGGATTTA
GGGGGCAACAACTTGCGCCACCTGACTGCACAGTCACTGCAGGGGCTGCC
CAAACTGCGCAGGCTGTACCTGGACCGCAACAGATTGCTGGAGGTGAGCA
GCACTGTGTTCGCCCCAGTGCAGGCTACCCTGGGGGTGCTGGACCTGCGG
GCCAACAACCTGCAGTACATCTCACAGTGGCTGCGCAAGCCGCCACCCTT
CCGCAACCTGAGCAGCCTGTACGACCTGAAGCTGCAGGCGCAGCAGCCCT
ATGGACTGAAGATGCTGCCTCACTACTTCTTCCAGGGCTTGGTGAGGCTA
CAGCAGCTGTCGCTGTCACAGAACATGCTGCGGTCCATCCCACCGGATGT

-continued

CTTCGAGGACTTGGGCCAGCTGCGCTCCCTGGCATTGGCTGACAGCAGCA
ATGGGCTGCATGACCTGCCTGACGGCATCTTCAGAAACCTGGGCAACCTG
CGGTTCCTGGACCTGGAGAATGCAGGGCTGCACTCGCTCACTCTGGAAGT
CTTCGGCAATCTCAGCCGGCTGCAGGTGCTGCACTTGGCCAGAAACGAGC
TGAAGACCTTCAATGACAGCGTTGCCAGCCGGCTGTCCTCCTTGCGCTAC
CTGGACCTGCGCAAGTGTCCGCTCAGCTGCACCTGTGACAACATGTGGCT
GCAGGGCTGGCTGAACAACAGCCGTGTGCAGGTTGTCTACCCCTACAACT
ACACCTGTGGCTCACAGCACAATGCCTACATCCACAGCTTTGACACACAC
GTCTGCTTCCTGGACCTGGGGCTCTATCTCTTTGCTGGGACTGCACCGGC
AGTGCTGCTGCTGCTGGTGGTGCCGGTGGTGTACCACCGCGCCTACTGGA
GGCTGAAGTACCACTGGTACCTTCTGCGGTGCTGGGTCAACCAGCGGTGG
CGGCGGGAGGAAAAGTGCTACCTCTATGACAGCTTTGTGTCCTACAATTC
AGCTGATGAAAGTTGGGTGTTGCAGAAGCTGGTGCCTGAGCTGGAGCACG
GTGCCTTCCGCCTCTGCTTGCACCACCGCGACTTCCAGCCGGGCCGCAGC
ATCATTGACAACATTGTGGATGCTGTCTACAACAGCCGGAAGACGGTGTG
CGTGGTGAGCCGCAGCTACCTGCGCAGCGAGTGGTGCTCTCTAGAGGTGC
AGTTGGCCAGCTACCGGCTGTTGGATGAGCGGCGTGACATCCTGGTACTG
GTGCTGCTGGAGGACGTGGGTGATGCTGAGCTGTCTGCCTACCACCGCAT
GCGGCGGGTGCTGCTGCGGCGCACCTACCTGCGCTGGCCTCTTGACCCCG
CAGCTCAGCCGCTCTTTTGGGCACGGCTGAAGAGGGCACTGAGGTGGGGA
GAGGGAGGAGAGGAGGAGGAAGAAGAAGGTTTGGGTGGAGGGACGGGAAG
GCCCAGGGAAGGAGACAAACAGATGTAGCGGCCGC

Transfection of HEK293-pNifTy2-Zeo (Clonal Cell Line) with pcDNA3.1(+)-Neo-chiTLR21

Human embryonic kidney (HEK) cells 293 have been generated in the 1970s by viral transformation (Graham et al., 1977), and are now available to the research community via cell line repositories, such as ATCC.

pNifty2 is a plasmid that allows the detection of NFκB transcription factor activation, which is a hallmark of many immunostimulatory actions, toll-like receptor activations amongst them. The reporter gene in pNifTy2 dependent in its transcription/translation on NFκB activation is secreted alkaline phosphatase (SEAP). Details are described in the datasheet of the company selling this plasmid: Invivogen. Transformation/transfection events by pNifty2 are selected in both bacteria and mammalian cells by zeocin addition to the growth media.

HEK293 cells were transfected with pNifTy2 by standard methods (lipofection), a stable cell line was selected, the functionality of the NF-κB/SEAP axis established by stimulation with human tumor necrosis factor α (Sigma). Secreted SEAP in the culture supernatant of stimulated cells was determined by a microtiter plate colorimetric assay employing the chromogenic substrate p-nitrophenylphosphate (pNPP, 5 mM) in an alkaline buffer (50 mM $NaHCO_3$, pH9.6, 2 mM $MgCl_2$). Colour development ($\lambda$=405 nm) was monitored by a microtiter plate reader. This readout was also used for selecting clonal lines (by the limiting dilution method) with high signal to noise ratios. One of these selected clones (dubbed clone 11) was then used for further studies with chicken TLR21.

pcDNA3.1(+)-neo is a standard mammalian expression vector purchased from Invitrogen. Subcloning of the chicken TLR21 gene into this vector was done via flanking Hind III (start codon) and Not I (stop codon) sites that were introduced by PCR. (See FIG. 1).

This plasmid was then transfected (lipofection) into the clonal HEK293-pNifTy2-zeo line, and recombinant cells were selected by addition of both zeocin and G418 into the growth medium. Functionality of the resulting polyclonal recombinant cell line was assessed by stimulation of the culture with ODN-X4 and ODN-HEK1-PTO and detection of SEAP. Superior clonal lines were then identified by the limiting dilution method followed by stimulation and SEAP detection.

SEAP is a reporter enzyme in mammalian systems (Yang et al., 1997). SEAP is a secreted form of human embryonic alkaline phosphatase. Its main advantages are the high stability and the extremely high specific activity, which ensure sensitivity and robustness of detection. Several substrates have been described for SEAP detection, but the economical and robust pNPP was selected, as its reaction product p-nitrophenolate is detected with high sensitivity ($\epsilon_{405}$=18500 $M^{-1}$ $cm^{-1}$). In our test setups, we perform kinetic assays, because they provide a wider dynamic range of quantification.

HEK293-pNifTy2-Zeo cells were transfected with pcDNA3.1(+)-Neo-chiTLR21 (linearized with Pvu I) and a polyclonal cell line was selected by supplementing the media with 350 µg/ml zeocin and 600 µg/ml G418. A functionality test was performed by stimulating the cells with ODN-X4 (PDE) and with ODN-HEK1 (PTO). Secreted alkaline phosphatase (SEAP) was produced by the selected cells, but not by the parental HEK293-pNifTy2-Zeo cell line. Single cell cloning was performed and individual clones were analyzed for their responsiveness to ODN-X4 (PDE) (GGGGGGT-TCGTTTTCGTTTTCGTTGGGGG) [SEQ ID NO: 23] and ODN-HEK1 (PTO) (TCGTCGTTTTGTCGTTTGTCGTT) [SEQ ID NO: 24].

Out of 46 zeo/G418-double-resistant clonal cell lines, only 3 were clearly responsive to the ODN stimuli, while 3-4 further cell lines showed weaker signals. 85% of the selected clones were, therefore, not functional.

For all further studies, clonal cell line 38, which produced by far the highest SEAP readout signal on response to ODN-X4 (PDE) and ODN-HEK1 (PTO) stimulation, was used.

FIGS. 2-5 give an overview of the SEAP activity of the various zeo/G418-double-resistant clonal cell lines.

Example 2

Starting from X43-batch4: GGGGGGTTCGTCT-TCGTCTTCGTCGGGGG [SEQ ID NO: 4], the following modifications were made and tested:

X43-I-T
[SEQ ID NO: 5]
GGGGGGTTTCGTCTTTTCGTCTTTTCGTCTGGGGG

X43-I-C
[SEQ ID NO: 6]
GGGGGGTTTCGTCCTTTCGTCCTTTCGTCCGGGGG

X43-II-T
[SEQ ID NO: 7]
GGGGGGTTTTCGTCTTTTTCGTCTTTTTCGTCTTGGGGG

X43-II-C
[SEQ ID NO: 8]
GGGGGGTTTTCGTCCCTTTTCGTCCCTTTTCGTCCGGGGG

X23-batch3
[SEQ ID NO: 9]
GGGGGGGTCGTCGTCGTCGTCGGGGG

X23-I
[SEQ ID NO: 10]
GGGGGGTGTCGTCTTGTCGTCTTGTCGTCTGGGGG

Figure 6:
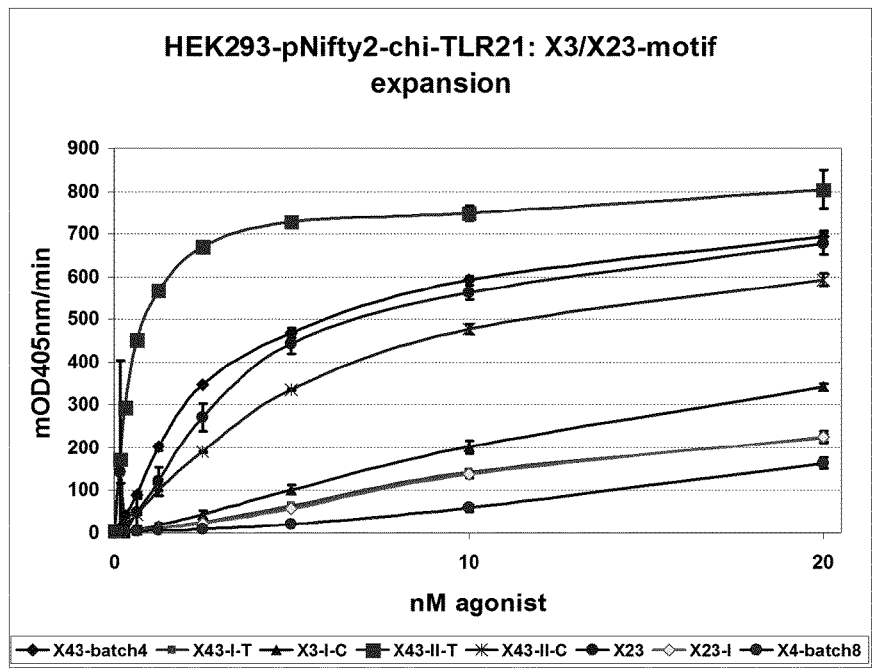

As can be seen from FIG. 6, oligonucleotide X43-II-T gives an extreme induction of the amount of the colored product absorbing at 405 nm of the reporter enzyme SEAP in the reporter cells (HEK293-pNifty2-chickenTLR21) with regard to maximal response, when compared to the other oligonucleotides tested.

X43-II-T represents the formula $^{5'}$ $[G]_x$ $\{[T]_p$ T T C G T C $[T]_q\}_n$ $[G]_z$ $^{3'}$ [SEQ ID NO: 25] wherein x=6, z=5, p=2, q=2 and n=3.

On the basis of FIG. 6, the following $EC_{50}$ calculation were made for the various compounds:

| $EC_{50}$ calculation: | X43-batch4 | 3.91 nM |
|---|---|---|
| | X43-I-T | >1200 nM |
| | X4-I-C | >300 nM |
| | X43-II-T | 0.53 nM |
| | X43-II-C | 8.28 nM |
| | X23-batch3 | 6.08 nM |
| | X23-I | >400 nM |

Figure 7:
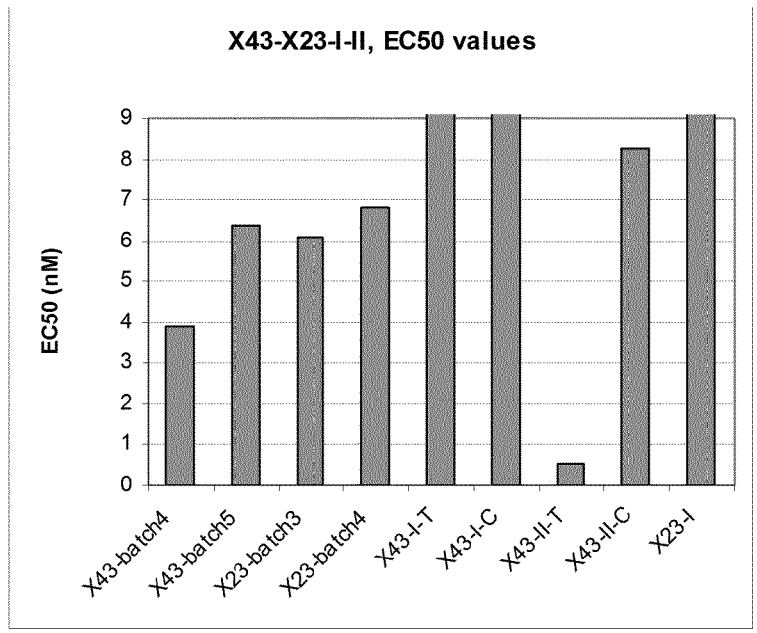

Conclusion: as follows from FIG. 6 representing the OD405 nm/min and FIG. 7 representing the $EC_{50}$ in nanomolar, the addition of two 3'-flanking thymidines and two 5'-flanking thymidines in X43 (→X43-II-T) leads to an unexpectedly strong increase of potency both with respect to maximal response and to $EC_{50}$. The $EC_{50}$ of the compound $^{5'}$ $[G]_6$ $\{[T]_2$ T T C G T C $[T]_2\}_3$ $[G]_5$ $^{3'}$ was shown to be in the picomolar range.

Example 3

In this Example, the number of n was varied from n=3 in X43-II-trip, to n=4 (X43-II-quad) and to n=5 (X43-II-pent)

```
X43-trip   5'-GGGGGGTTCGTCTTCGTCTTCGTCGGGGG-3'+0 (= standard 1) [SEQ ID NO: 11]

X4-pent    5'-GGGGGGTTCGTTTTCGTTTTCGTTTTCGTTTTCGTTGGGGG-3' [SEQ ID NO: 12]
           (= standard 2)

X43-II-trip 5'-GGGGGGTTTTCGTCTTTTTCGTCTTTTTCGTCTTGGGGG-3' [SEQ ID NO: 13]
           (n = 3, and with [p and q] = 2)
```

-continued

```
X43-II-quad 5'-GGGGGGTTTTCGTCTTTTTTCGTCTTTTTTCGTCTTTTTTCGTCTTGGGGG-3'
            [SEQ ID NO: 14]
            n = 4, and with [p and q] = 2)

X43-II-pent 5'-GGGGGGTTTTCGTCTTTTTTCGTCTTTTTTCGTCTTTTTTCGTCTTTTTTCGTCTTGGGGG-3'
            [SEQ ID NO: 15]
            n = 5, and with [p and q] = 2)
```

Figure 8:
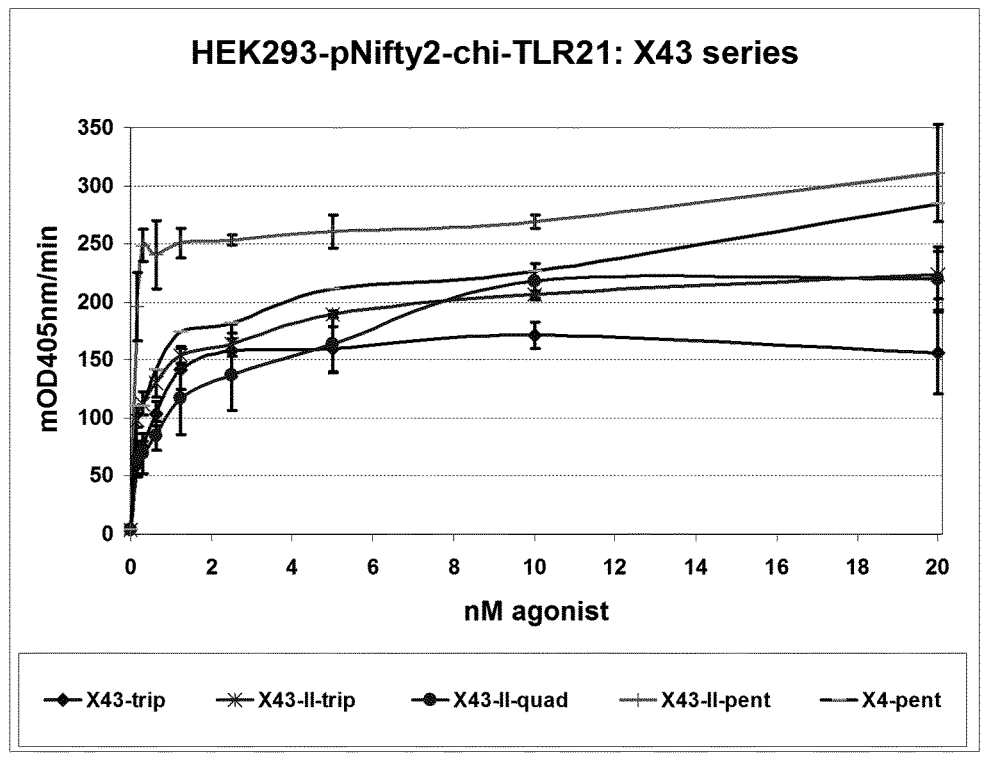

In FIG. 8, the effect of the increase in the number of n is shown. In the table below, the effect of an increase in n on the $EC_{50}$ is shown. It is clear that an increase in n leads to a decrease in $EC_{50}$ and thus to a higher immunostimulatory effect.

| ODN | $EC_{50}$ |
|---|---|
| X43-trip | 338 pM |
| X43-II-trip | 155 pM |
| X43-II-quad | 132 pM |
| X43-II-pent | 59 pM |
| X4-pent | 340 pM |

Example 4

In this Example, the number of p and q was changed from 2 (X43-II-trip) to 3 (X43-III-trip) and to 4 (X43-IV-trip)

```
X43-I-trip    5'-GGGGGGTTCGTCTTCGTCTTCGTCGGGGG-3' (= standard 1)
              (n = 3, and with [p and q] = 0)

X4-pent       5'-GGGGGGTTCGTTTTCGTTTTCGTTTTCGTTGGGGG-3'
              (= standard 2)

X43-II-trip   5'-GGGGGGTTTTCGTCTTTTTTCGTCTTTTTTCGTCTTGGGGG-3'
              (n = 3, and with [p and q] = 2)

X43-III-trip  5'-GGGGGGTTTTCGTCTTTTTTTCGTCTTTTTTTCGTCTTTGGGGG-3'
              (n = 3, and with [p and q] = 3)

X43-IV-trip   5'-GGGGGGTTTTTCGTCTTTTTTTTCGTCTTTTTTTTCGTCTTTTGGGGG-3'
              (n = 3, and with [p and q] = 4)
```

Figure 9:
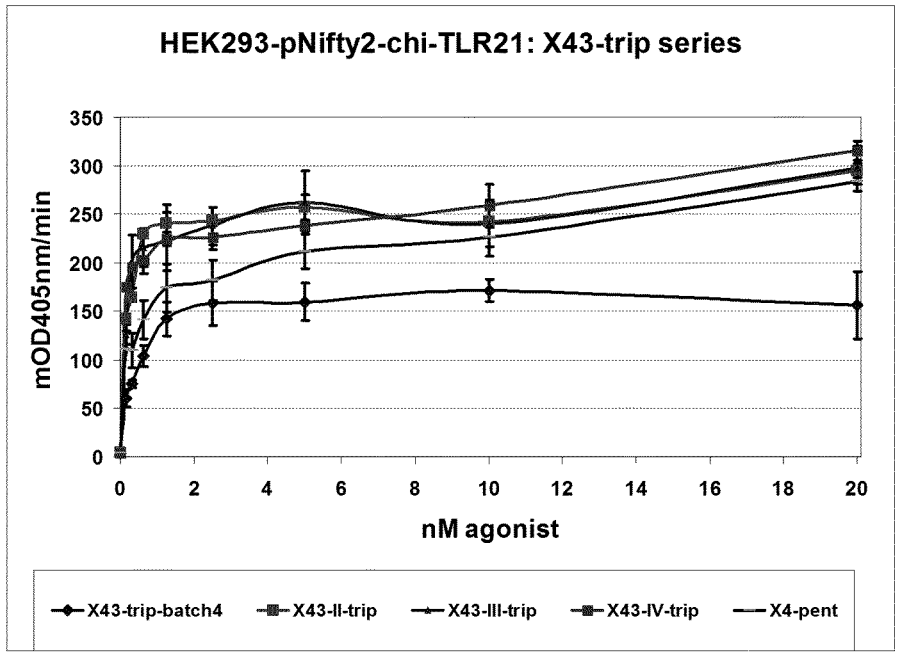

In FIG. 9, the effect of the increase in the number of p and q is shown. In the table below, the effect of an increase in n on the $EC_{50}$ is shown. It is clear that an increase in p and q leads to a decrease in $EC_{50}$ and thus to a higher immunostimulatory effect.

| ODN | $EC_{50}$ |
|---|---|
| X43-trip | 338 pM |
| X43-II-trip | 155 pM |
| X43-III-trip | 148 pM |
| X23-IV-trip | 104 pM |
| X4-pent | 340 pM |

Example 5

In this Example, the number of x was increased from 6 to 7 (X43-II-5735) and z was decreased from 5 to 2 (X43-II-5732).

```
X43-II       5'-GGGGGGTTTTCGTCTTTTTTCGTCTTTTTTCGTCTT
             GGGGG-3'
             (= standard 1, X43-II-trip)
             [SEQ ID NO: 13]

X4-pent      5'-GGGGGGTTCGTTTTCGTTTTCGTTTTCGTT
             GGGGG-3'
             (= standard 2)[SEQ ID NO: 12]

X43-II-5735  5'-GGGGGGGTTTTCGTCTTTTTTCGTCTTTTTTCGTCTT
             GGGGG-3'[SEQ ID NO: 19]
             (→ x = 7, z = 5, p and q both = 2 and
             n = 3)

X43-II-5732  5'-GGGGGGGTTTTCGTCTTTTTTCGTCTTTTTTCGTCTT
             GG-3' [SEQ ID NO: 20]
             (→ x = 7, z = 2, p and q both = 2 and
             n = 3)
```

Figure 10:
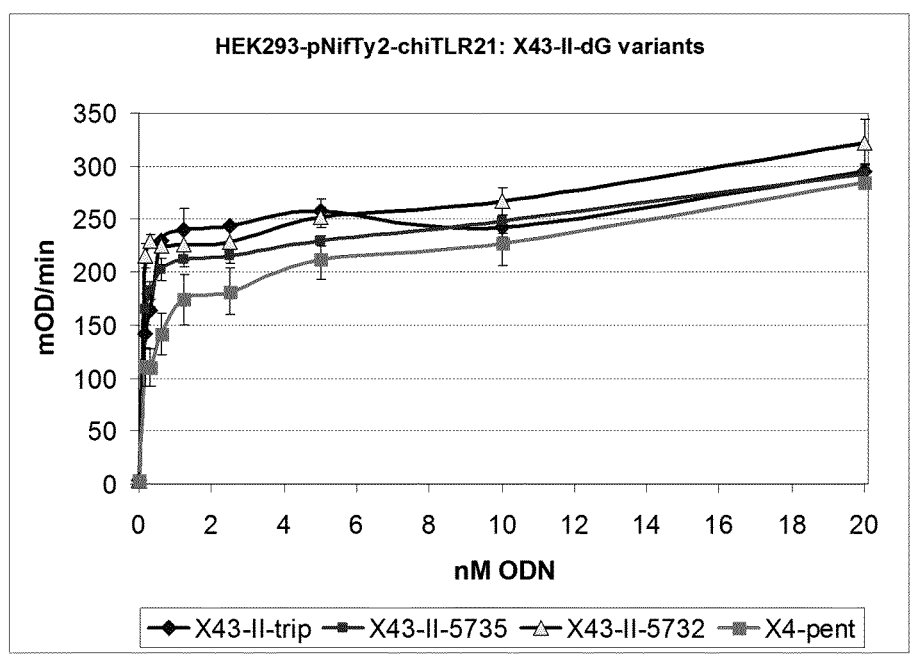

In FIG. 10, the effect of the increase in the number of x and the decrease in the number of z is shown. In the table below, the effect of an increase in n on the $EC_{50}$ is shown. An increase of x and a decrease of z both lead to an increase in EC50 and thus to a higher immunostimulatory effect.

| ODN | $EC_{50}$ |
|---|---|
| X43-II-trip | 155 pM |
| X43-II-5735 | 105 pM |
| X23-II-5732 | <<100 pM |
| X4-pent | 340 pM |

LEGEND TO THE FIGURES

FIG. 1: Plasmid map of pcDNA3.1(+)-chiTLR21

FIG. 2-5: overview of the SEAP activity of the various zeo/G418-double-resistant clonal cell lines.

FIG. 6: this figure shows the strength of the various compounds tested, in inducing an amount of the colored product absorbing at 405 nm of the reporter enzyme SEAP in the reporter cells (HEK293-pNifty2-chickenTLR21)

FIG. 7: this figure shows the $EC_{50}$ values of the various compounds tested, in picomoles.

FIGS. 8-10: these figures show the strength of further modified compounds tested, in inducing an amount of the colored product absorbing at 405 nm of the reporter enzyme SEAP in the reporter cells (HEK293-pNifty2-chickenTLR21).

LITERATURE REFERENCES

Babiuk L. A., Gomis S., Hecker R., 2003. Molecular approaches to disease control. *Poult. Sci.* 82, 870-875.

Brownlie, R., Zhu J., Allan B., Mutwiri G. K., Babiuk L. A., Potter A., Griebel P., 2009. Chicken TLR21 acts as a functional homologue to mammalian TLR9 in the recognition of CpG oligodeoxynucleotides. *Mol. Immunol.* 46, 3163-3170

Carrington A. C., Secombes C. J., 2006. A review of CpGs and their relevance to aquaculture. *Vet. Immunol. Immunopathol.* 112, 87-101.

Daubenberger C. A., 2007. TLR9 agonists as adjuvants for prophylactic and therapeutic vaccines. *Curr. Opin. Mol. Ther.* 9, 45-52.

Dorn A., Kippenberger S., 2008. Clinical application of CpG-, non-CpG-, and antisense oligodeoxynucleotides as immunomodulators. *Curr. Opin. Mol. Ther.* 10, 10-20.

Fonseca D. E., Kline J. N., 2009. Use of CpG oligodeoxynucleotides in treatment of asthma and allergic disease. *Adv. Drug Deliv. Rev.* 61, 256-262.

Graham, F. L., Smiley, J., Russell, W. C., Nairn, R., 1977. Characteristics of a human cell line transformed by DNA from human adenovirus type 5. *J. Gen. Virol.* 36, 59-74.

Griebel P. J., Brownlie R., Manuja A., Nichani A., Mookherjee N., Popowych Y., Mutwiri G., Hecker R., Babiuk L. A., 2005. Bovine toll-like receptor 9: a comparative analysis of molecular structure, function and expression. *Vet. Immunol. Immunopathol.* 108, 11-16.

Hemmi H., Takeuchi O., Kawai T., Kaisho T., Sato S., Sanjo H., Matsumoto M., Hoshino K., Wagner H., Takeda K., Akira S., 2000. A Toll-like receptor recognizes bacterial DNA. *Nature* 408, 740-745.

Iwasaki A, Medzhitov R. Regulation of adaptive immunity by the innate immune system. 2010. *Science* 327, 291-295.

Keestra A. M., 2008. Molecular dissection of the chicken Toll-like receptor repertoire. PhD thesis (Proefschrift), University of Utrecht, The Netherlands Kline J. N., 2007. Immunotherapy of asthma using CpG oligodeoxynucleotides. *Immunol. Res.* 39, 279-286.

Kline J. N., Krieg A. M., 2008. Toll-like receptor 9 activation with CpG oligodeoxynucleotides for asthma therapy. *Drug News Perspect.* 21, 434-439.

Klinman D. M., 2004. Immunotherapeutic uses of CpG oligodeoxynucleotides. *Nat. Rev. Immunol.* 4, 249-258.

Klinman D. M, Currie D., Gursel I., Verthelyi D., 2004. Use of CpG oligodeoxynucleotides as immune adjuvants. *Immunol. Rev.* 199, 201-216.

Klinman D. M., 2006. Adjuvant activity of CpG oligodeoxynucleotides. Int. Rev. *Immunol.* 25, 135-154.

Klinman D. M., Klaschik S., Sato T., Tross D., 2009. CpG oligodeoxynucleotides as adjuvants for vaccines targeting infectious diseases. *Adv. Drug Deliv. Rev.* 61, 248-255.

Kindrachuk J., Potter J., Wilson H. L., Griebel P., Babiuk L. A., Napper S., 2008. Activation and regulation of toll-like receptor 9: CpGs and beyond. *Mini Rev. Med. Chem.* 8, 590-600.

Krieg A. M., Yi A, K., Matson S., Waldschmidt T, J., Bishop G. A., Teasdale R., Koretzky G. A., Klinman D. M., 1995. CpG motifs in bacterial DNA trigger direct B-cell activation. *Nature* 374, 546-549.

Krieg A. M., 2002. CpG motifs in bacterial DNA and their immune effects. *Annu. Rev. Immunol.* 20, 709-760.

Krieg A. M., 2003. CpG motifs: the active ingredient in bacterial extracts? *Nat. Med.* 9, 831-835.

Krieg A. M., 2006. Therapeutic potential of Toll-like receptor 9 activation. *Nat. Rev. Drug Discov.* 5, 471-484.

Krieg A. M., 2007a. Anti-infective applications of toll-like receptor 9 agonists. *Proc. Am. Thorac. Soc.* 4, 289-294.

Krieg A. M., 2007b. Development of TLR9 agonists for cancer therapy. *J. Clin. Invest.* 117, 1184-1194.

Linghua Zhang et al., 2007. Vaccination with Newcatle disease vaccine and CpG oligodeoxynucleotides induces specific immunity and protection against Newcastle disease virus in SPF chicken. *Vet. Immun. And Immunopath.* 115, 216-222.

Medzhitov R., 2001. CpG DNA: security code for host defense. *Nat. Immunol.* 2, 15-16.

Medzhitov R., Approaching the asymptote: 20 years later. 2009. *Immunity* 30, 766-775)

Mutwiri G., van Drunen Littel-van den Hurk S., Babiuk L. A., 2009. Approaches to enhancing immune responses stimulated by CpG oligodeoxynucleotides. *Adv. Drug Deliv. Rev.* 61, 226-232.

Mutwiri G., Pontarollo R., Babiuk S., Griebel P., van Drunen Littel-van den Hurk S., Mena A., Tsang C., Alcon V., Nichani A., Ioannou X., Gomis S., Townsend H., Hecker R., Potter A., Babiuk L. A., 2003. Biological activity of immunostimulatory CpG DNA motifs in domestic animals. Vet. Immunol Immunopathol. 91, 89-103.

Schindler, U., and Baichwal, V. R., 1994. Moll. Cell. Biol. 14: 5820-5831.

Singh M., O'Hagan D. T., 2003. Recent advances in veterinary vaccine adjuvants. *Int. J. Parasitol.* 33, 469-478.

Vollmer J., 2005. Progress in drug development of immunostimulatory CpG oligodeoxynucleotide ligands for TLR9. *Expert Opin. Biol. Ther.* 5, 673-682.

Vollmer J., Krieg A. M., 2009 Immunotherapeutic applications of CpG oligodeoxynucleotide TLR9 agonists. *Adv. Drug Deliv. Rev.* 61, 195-204.

Wagner H., 2009. The immunogenicity of CpG-antigen conjugates. *Adv. Drug. Deliv. Rev.* 61, 243-247.

Weiner G. J., 2009. CpG oligodeoxynucleotide-based therapy of lymphoid malignancies. *Adv. Drug Deliv. Rev.* 61, 263-267.

Werling D., Jungi T. W., 2003. TOLL-like receptors linking innate and adaptive immune response. *Vet. Immunol. Immunopathol.* 91, 1-12.

Wilson H. L., Dar A., Napper S. K., Marianela Lopez A., Babiuk L. A., Mutwiri G. K., 2006. Immune mechanisms and therapeutic potential of CpG oligodeoxynucleotides. *Int. Rev. Immunol.* 25, 183-213.

Wilson K. D., de Jong S. D., Tam Y. K., 2009. Lipid-based delivery of CpG oligodeoxynucleotides enhances immunotherapeutic efficacy. *Adv. Drug Deliv. Rev.* 61, 233-242.

Yang, T. T., Sinai, P., Kitts, P. A., Kain, S. R., 1997. Quantification of gene expression with a secreted alkaline phosphatase reporter system. *Biotechniques* 23, 1110-1114.

The invention claimed is:

1. An immunostimulatory non-methylated oligodeoxynucleotide having the general formula $^{5'}[G]_x\{[T]_p\,T\,T\,C\,G\,T\,C\,[T]_q\}_n\,[G]_z\,^{3'}$ [SEQ ID NO: 25]

wherein p=1-6, q=1-6, n=2-18, x=3-10 and z=0-10 or a pharmaceutically acceptable salt thereof.

2. The oligodeoxynucleotide according to claim 1, wherein p>1.

3. The oligodeoxynucleotide according to claim 1, wherein p>2.

4. The oligodeoxynucleotide according to claim 1, wherein q>1.

5. The oligodeoxynucleotide according to claim 1, wherein q>2.

6. The oligodeoxynucleotide according to claim 1, wherein n=3-18.

7. The oligodeoxynucleotide according to claim 1, characterised in that the $^{5'}[G]_x$ and the $^{3'}[G]_z$ nucleotides have a phosphorothioate binding and the other nucleotides have a phosphodiester binding.

8. The oligodeoxynucleotide according to claim 1, wherein $\{[T]_p\,T\,T\,C\,G\,T\,C\,[T]_q\}_n$ [SEQ ID NO: 26] is a homopolymer.

9. The oligodeoxynucleotide according to claim 1, wherein said oligodeoxynucleotide is coupled to a carrier or hapten.

10. A vector comprising the oligodeoxynucleotide according to claim 1.

11. A vaccine for preventing or combating an infectious disease, characterised in that said vaccine comprises an immunostimulatory amount of an oligodeoxynucleotide according to claim 1, an immunological amount of an antigen component or genetic information encoding an antigen component, and a pharmaceutically acceptable carrier.

12. The vaccine according to claim 11, characterised in that said antigen component is, or is derived from a virus or micro-organism that in its wild-type form is pathogenic to poultry.

13. The vaccine according to claim 12 characterised in that said virus or micro-organism is selected from the group consisting of an Infectious Bronchitis virus, a Newcastle Disease virus, an Infectious Bursal Disease (Gumboro), a Chicken Anaemia agent, an Avian Reovirus, a *Mycoplasma gallisepticum*, a Turkey Rhinotracheitis virus, an *Haemophilus paragallinarum* (Coryza), a Chicken Poxvirus, an Avian Encephalomyelitis virus, an Egg Drop syndrome virus, an Infectious Laryngotracheitis virus, a Herpesvirus of Turkeys, an Eimeria species, an *Ornithobacterium rhinotracheale*, a *Pasteurella multocida*, a *Mycoplasma synoviae*, a *Salmonella* species and an *E. coli*.

14. A vaccine for preventing or combating an infectious disease, characterised in that said vaccine comprises a vector comprising the oligodeoxynucleotide according to claim 1, an immunological amount of an antigen component or genetic information encoding an antigen component, and a pharmaceutically acceptable carrier.

15. A vaccine for preventing or combating an infectious disease, characterised in that said vaccine comprises a vector comprising the oligodeoxynucleotide according to claim 1, an immunological amount of an antigen component or genetic information encoding an antigen component, and a pharmaceutically acceptable carrier, wherein said antigen component is, or is derived from a virus or micro-organism that in its wild-type form is pathogenic to poultry.

16. A vaccine for preventing or combating an infectious disease, characterised in that said vaccine comprises a vector comprising the oligodeoxynucleotide according to claim 1, an immunological amount of an antigen component or genetic information encoding an antigen component, and a pharmaceutically acceptable carrier, wherein said antigen component is, or is derived from a virus or micro-organism that in its wild-type form is pathogenic to poultry, and wherein said virus or micro-organism is selected from the group consisting of an Infectious Bronchitis virus, a Newcastle Disease virus, an Infectious Bursal Disease (Gumboro), a Chicken Anaemia agent, an Avian Reovirus, a *Mycoplasma gallisepticum*, a Turkey Rhinotracheitis virus, an *Haemophilus paragallinarum* (Coryza), a Chicken Poxvirus, an Avian Encephalomyelitis virus, an Egg Drop syndrome virus, an Infectious Laryngotracheitis virus, a Herpesvirus of Turkeys, an Eimeria species, an *Ornithobacterium rhinotracheale*, a *Pasteurella multocida*, a *Mycoplasma synoviae*, a *Salmonella* species and an *E. coli*.

17. A medicament that comprises a vector comprising the oligodeoxynucleotide of claim 1 in combination with an immunological amount of an antigenic component or genetic information encoding an antigenic component;
wherein said antigenic component is, or is derived from, a virus or micro-organism that in its wild-type form is pathogenic to poultry.

18. A method of preventing infection in poultry that comprises administering to poultry the medicament of claim 17.

* * * * *

SEQUENCE LISTING

<160> NUMBER OF SEQ ID NOS: 26

<210> SEQ ID NO 1
<211> LENGTH: 33
<212> TYPE: DNA
<213> ORGANISM: artificial sequence
<220> FEATURE:
<223> OTHER INFORMATION: synthetic DNA

<400> SEQUENCE: 1
gaagcttacc atgatggaga cagcggagaa ggc        33

<210> SEQ ID NO 2
<211> LENGTH: 33
<212> TYPE: DNA
<213> ORGANISM: artificial sequence
<220> FEATURE:
<223> OTHER INFORMATION: synthetic DNA

<400> SEQUENCE: 2
ggcggccgct acatctgttt gtctccttcc ctg        33

<210> SEQ ID NO 3
<211> LENGTH: 2935
<212> TYPE: DNA
<213> ORGANISM: artificial sequence
<220> FEATURE:
<223> OTHER INFORMATION: synthetic DNA

<400> SEQUENCE: 3

| | | | | | |
|---|---|---|---|---|---|
| aagcttacca | tgatggagac | agcggagaag | gcatggccca | gcaccaggat | gtgcccctcc | 60 |
| cactgctgtc | cactctggct | gctgctgctg | gtgacagtga | cactgatgcc | gatggtgcac | 120 |
| ccgtatggct | ttcgcaactg | cattgaggat | gtcaaggcac | ctttgtactt | ccgctgcatc | 180 |
| cagcgcttcc | tgcagtcgcc | ggccctggca | gtgtctgacc | tgccaccaca | tgccatcgcg | 240 |
| ctcaatctgt | catacaacaa | aatgcgctgc | ctgcagccct | ctgcctttgc | ccacctgaca | 300 |
| cagctgcata | ccctggacct | gacctacaac | ctcctggaga | ccctctcccc | tggtgccttc | 360 |
| aatgggctgg | gtgtgctggt | ggtgctggac | ctgtctcaca | caagctgac | cacacttgct | 420 |
| gaaggggtgt | tcaacagctt | gggcaacctg | tcctcgctgc | aggtacaaca | taaccccctc | 480 |
| agcacggtgt | caccaagtgc | tctgctaccc | ctggtcaacc | tgcgccgcct | gtctctacgg | 540 |
| ggcgggcggc | tgaatgggtt | ggggggcagtg | gcagtggcag | tgcagggctt | ggcacagctg | 600 |
| gagctgttgg | acctatgtga | aaacaacctg | acaacgctgg | ggccaggccc | accgctaccc | 660 |
| gcctcgctgc | tcaccctgca | gctgtgcaac | aactcgctga | gggagttagc | ggggggcagc | 720 |
| ccggagatgc | tatggcacgt | gaagatactc | gacctctcct | acaacagtat | ctcacaggcg | 780 |
| gaggtcttca | cccagctcca | cctgcgcaac | atcagcctgc | tccacctgat | cggcaacccc | 840 |
| ttggatgtct | tccacctgtt | ggacatctct | gacatccaac | ctcgcagcct | ggatttctct | 900 |
| gggttggtgc | tgggggctca | ggggctggat | aaggtgtgcc | tgaggctgca | gggtccccag | 960 |
| gccttgcggg | gctgcagct | acaacgcaac | gggctgaagg | tgctgcattg | taatgcactg | 1020 |
| cagttgtgtc | ctgtgctgag | agagctggac | ctgtcctgga | accggctaca | gcacgtgggc | 1080 |
| tgtgccggcc | ggctgctggg | caagaagcag | cgggagaagc | tggaagtgct | gacagtggaa | 1140 |
| cacaacctgc | tgaagaaact | gccgtcttgc | ctggggccc | aggtgctgcc | tcggctgtac | 1200 |
| aacatttcct | tccgctttaa | ccgcatcctg | actgttgggc | cccaagcctt | tgcctacgcc | 1260 |
| ccggccctgc | aggtgttgtg | gctcaatatt | aacagcctgg | tgtggctgga | caggcaggca | 1320 |

| | |
|---|---|
| ctgtggaggc tgcacaacct gacagagctg cgcctggaca acaacctgct gaccgacctc | 1380 |
| tatcacaact ccttcattga cctccacaga ctgcgcaccc tcaacctgcg caacaaccgt | 1440 |
| gtctccgtcc tcttctctgg tgtcttccag gggctggctg agctgcagac gctggattta | 1500 |
| gggggcaaca acttgcgcca cctgactgca cagtcactgc aggggctgcc caaactgcgc | 1560 |
| aggctgtacc tggaccgcaa cagattgctg gaggtgagca gcactgtgtt cgccccagtg | 1620 |
| caggctaccc tggggtgct ggacctgcgg gccaacaacc tgcagtacat ctcacagtgg | 1680 |
| ctgcgcaagc cgccacccct ccgcaacctg agcagcctgt acgacctgaa gctgcaggcg | 1740 |
| cagcagccct atggactgaa gatgctgcct cactacttct tccagggctt ggtgaggctg | 1800 |
| cagcagctgt cgctgtcaca gaacatgctg cggtccatcc caccggatgt cttcgaggac | 1860 |
| tgggccagc tgcgctccct ggcattggct gacagcagca atgggctgca tgacctgcct | 1920 |
| gacggcatct tcagaaacct gggcaacctg cggttcctgg acctggagaa tgcagggctg | 1980 |
| cactcgctca ctctggaagt cttcggcaat ctcagccggc tgcaggtgct gcacttggcc | 2040 |
| agaaacgagc tgaagacctt caatgacagc gttgccagcc ggctgtcctc cttgcgctac | 2100 |
| ctggacctgc gcaagtgtcc gctcagctgc acctgtgaca catgtggct gcagggctgg | 2160 |
| ctgaacaaca gccgtgtgca ggttgtctac ccctacaact acacctgtgg ctcacagcac | 2220 |
| aatgcctaca tccacagctt tgacacacac gtctgcttcc tggacctggg gctctatctc | 2280 |
| tttgctggga ctgcaccggc agtgctgctg ctgctggtgg tgccggtggt gtaccaccgc | 2340 |
| gcctactgga ggctgaagta ccactggtac cttctgcggt gctgggtcaa ccagcggtgg | 2400 |
| cggcgggagg aaaagtgcta cctctatgac agctttgtgt cctacaattc agctgatgaa | 2460 |
| agttgggtgt tgcagaagct ggtgcctgag ctggagcacg tgccttccg cctctgcttg | 2520 |
| caccaccgcg acttccagcc gggccgcagc atcattgaca acattgtgga tgctgtctac | 2580 |
| aacagccgga agacggtgtg cgtggtgagc cgcagctacc tgcgcagcga gtggtgctct | 2640 |
| ctagaggtgc agttggccag ctaccgctg ttggatgagc ggcgtgacat cctggtactg | 2700 |
| gtgctgctgg aggacgtggg tgatgctgag ctgtctgcct accaccgcat gcggcgggtg | 2760 |
| ctgctgcggc gcacctacct cgctggcct cttgaccccg cagctcagcc gctcttttgg | 2820 |
| gcacggctga gagggcact gaggtgggga gagggaggag aggaggagga agaagaaggt | 2880 |
| ttgggtggag ggacgggaag gcccagggaa ggagacaaac agatgtagcg gccgc | 2935 |

<210> SEQ ID NO 4
<211> LENGTH: 29
<212> TYPE: DNA
<213> ORGANISM: artificial sequence
<220> FEATURE:
<223> OTHER INFORMATION: synthetic DNA

<400> SEQUENCE: 4 gggggggttcg tcttcgtctt cgtcggggg                                29

<210> SEQ ID NO 5
<211> LENGTH: 35
<212> TYPE: DNA
<213> ORGANISM: artificial sequence
<220> FEATURE:
<223> OTHER INFORMATION: synthetic DNA

<400> SEQUENCE: 5 gggggggtttc gtctttcgt cttttcgtct ggggg                          35

<210> SEQ ID NO 6
<211> LENGTH: 35
<212> TYPE: DNA
<213> ORGANISM: artificial sequence
<220> FEATURE:
<223> OTHER INFORMATION: synthetic DNA

<400> SEQUENCE: 6 gggggtttc gtcctttcgt cctttcgtcc ggggg             35

<210> SEQ ID NO 7
<211> LENGTH: 41
<212> TYPE: DNA
<213> ORGANISM: artificial sequence
<220> FEATURE:
<223> OTHER INFORMATION: synthetic DNA

<400> SEQUENCE: 7
gggggttttt cgtctttttt cgtctttttt cgtcttgggg g             41

<210> SEQ ID NO 8
<211> LENGTH: 41
<212> TYPE: DNA
<213> ORGANISM: artificial sequence
<220> FEATURE:
<223> OTHER INFORMATION: synthetic DNA

<400> SEQUENCE: 8
ggggggtttt cgtcccttt cgtcccttt cgtcccgggg g             41

<210> SEQ ID NO 9
<211> LENGTH: 29
<212> TYPE: DNA
<213> ORGANISM: artificial sequence
<220> FEATURE:
<223> OTHER INFORMATION: synthetic DNA

<400> SEQUENCE: 9 ggggggtcg tcgtcgtcgt cgtcggggg             29

<210> SEQ ID NO 10
<211> LENGTH: 35
<212> TYPE: DNA
<213> ORGANISM: artificial sequence
<220> FEATURE:
<223> OTHER INFORMATION: synthetic DNA

<400> SEQUENCE: 10 gggggtgtc gtcttgtcgt cttgtcgtct ggggg             35

<210> SEQ ID NO 11
<211> LENGTH: 29
<212> TYPE: DNA
<213> ORGANISM: artificial sequence
<220> FEATURE:
<223> OTHER INFORMATION: synthetic DNA

<400> SEQUENCE: 11 gggggttcg tcttcgtctt cgtcggggg             29

<210> SEQ ID NO 12
<211> LENGTH: 41
<212> TYPE: DNA
<213> ORGANISM: artificial sequence
<220> FEATURE:
<223> OTHER INFORMATION: synthetic DNA

```
<400> SEQUENCE: 12 gggggggttcg ttttcgtttt cgttttcgtt ttcgttgggg g                41

<210> SEQ ID NO 13
<211> LENGTH: 41
<212> TYPE: DNA
<213> ORGANISM: artificial sequence
<220> FEATURE:
<223> OTHER INFORMATION: synthetic DNA

<400> SEQUENCE: 13 gggggggtttt cgtcttttttt cgtcttttttt cgtcttgggg g              41

<210> SEQ ID NO 14
<211> LENGTH: 51
<212> TYPE: DNA
<213> ORGANISM: artificial sequence
<220> FEATURE:
<223> OTHER INFORMATION: synthetic DNA

<400> SEQUENCE: 14 gggggggtttt cgtcttttttt cgtcttttttt cgtcttttttt cgtcttgggg g   51

<210> SEQ ID NO 15
<211> LENGTH: 61
<212> TYPE: DNA
<213> ORGANISM: artificial sequence
<220> FEATURE:
<223> OTHER INFORMATION: synthetic DNA

<400> SEQUENCE: 15 gggggggtttt cgtcttttttt cgtcttttttt cgtcttttttt cgtcttttttt cgtcttgggg   60 g                                                              61

<210> SEQ ID NO 16
<211> LENGTH: 29
<212> TYPE: DNA
<213> ORGANISM: artificial sequence
<220> FEATURE:
<223> OTHER INFORMATION: synthetic DNA

<400> SEQUENCE: 16 gggggggttcg tcttcgtctt cgtcggggg                              29

<210> SEQ ID NO 17
<211> LENGTH: 47
<212> TYPE: DNA
<213> ORGANISM: artificial sequence
<220> FEATURE:
<223> OTHER INFORMATION: synthetic DNA

<400> SEQUENCE: 17 gggggggtttt tcgtcttttt tttcgtcttt tttttcgtct ttgggg           47

<210> SEQ ID NO 18
<211> LENGTH: 53
<212> TYPE: DNA
<213> ORGANISM: artificial sequence
<220> FEATURE:
<223> OTHER INFORMATION: synthetic DNA

<400> SEQUENCE: 18 ggggggggtttt ttcgtcttttt tttttcgtc ttttttttttt cgtctttttgg ggg  53
```

```
<210> SEQ ID NO 19
<211> LENGTH: 42
<212> TYPE: DNA
<213> ORGANISM: artificial sequence
<220> FEATURE:
<223> OTHER INFORMATION: synthetic DNA

<400> SEQUENCE: 19
ggggggtttt tcgtcttttt tcgtcttttt tcgtcttggg gg                            42

<210> SEQ ID NO 20
<211> LENGTH: 39
<212> TYPE: DNA
<213> ORGANISM: artificial sequence
<220> FEATURE:
<223> OTHER INFORMATION: synthetic DNA

<400> SEQUENCE: 20
gggggggttt tcgtcttttt tcgtcttttt tcgtcttgg                               39

<210> SEQ ID NO 21
<211> LENGTH: 10
<212> TYPE: DNA
<213> ORGANISM: artificial sequence
<220> FEATURE:
<223> OTHER INFORMATION: synthetic DNA

<400> SEQUENCE: 21
gtttcgtctg                                                               10

<210> SEQ ID NO 22
<211> LENGTH: 24
<212> TYPE: DNA
<213> ORGANISM: artificial sequence
<220> FEATURE:
<223> OTHER INFORMATION: synthetic DNA

<400> SEQUENCE: 22
tttcgtcttt tcgtcttttc gtct                                               24

<210> SEQ ID NO 23
<211> LENGTH: 29
<212> TYPE: DNA
<213> ORGANISM: artificial sequence
<220> FEATURE:
<223> OTHER INFORMATION: synthetic DNA

<400> SEQUENCE: 23 gggggttcg ttttcgtttt cgttggggg                                           29

<210> SEQ ID NO 24
<211> LENGTH: 23
<212> TYPE: DNA
<213> ORGANISM: artificial sequence
<220> FEATURE:
<223> OTHER INFORMATION: synthetic DNA

<400> SEQUENCE: 24
tcgtcgtttt gtcgtttgtc gtt                                                23

<210> SEQ ID NO 25
<211> LENGTH: 344
<212> TYPE: DNA
```

-continued

```
<213> ORGANISM: artificial sequence
<220> FEATURE:
<223> OTHER INFORMATION: synthetic DNA
<220> FEATURE:
<221> NAME/KEY: misc_feature
<222> LOCATION: (1)..(10)
<223> OTHER INFORMATION: Number of G's may vary between 3 and 10
<220> FEATURE:
<221> NAME/KEY: misc_feature
<222> LOCATION: (11)..(28)
<223> OTHER INFORMATION: number of repeats ttttttttcgtctttttt may vary
      between 2 and 18
<220> FEATURE:
<221> NAME/KEY: misc_feature
<222> LOCATION: (11)..(16)
<223> OTHER INFORMATION: Number of T's may vary between 1 and 6
<220> FEATURE:
<221> NAME/KEY: misc_feature
<222> LOCATION: (23)..(28)
<223> OTHER INFORMATION: Number of T's may vary between 1 and 6
<220> FEATURE:
<221> NAME/KEY: misc_feature
<222> LOCATION: (335)..(344)
<223> OTHER INFORMATION: Number of G's may vary between 0 and 10

<400> SEQUENCE: 25
gggggggggg ttttttttcg tctttttttt ttttttcgtc tttttttttt ttttcgtctt      60
tttttttttt ttcgtctttt tttttttttt cgtctttttt tttttttcg tctttttttt     120 ttttttcgtc tttttttttt ttttcgtctt tttttttttt ttcgtctttt tttttttttt     180
cgtctttttt tttttttcg tctttttttt ttttttcgtc tttttttttt ttttcgtctt     240
tttttttttt ttcgtctttt tttttttttt cgtctttttt tttttttcg tctttttttt     300 ttttttcgtc tttttttttt ttttcgtctt ttttggggg gggg                      344

<210> SEQ ID NO 26
<211> LENGTH: 344
<212> TYPE: DNA
<213> ORGANISM: artificial sequence
<220> FEATURE:
<223> OTHER INFORMATION: synthetic DNA
<220> FEATURE:
<221> NAME/KEY: misc_feature
<222> LOCATION: (11)..(334)
<223> OTHER INFORMATION: all repeats are identical
<220> FEATURE:
<221> NAME/KEY: misc_feature
<222> LOCATION: (11)..(16)
<223> OTHER INFORMATION: Number of T's may vary between 1-6
<220> FEATURE:
<221> NAME/KEY: misc_feature
<222> LOCATION: (23)..(28)
<223> OTHER INFORMATION: Number of T's may vary between 1-6

<400> SEQUENCE: 26
gggggggggg ttttttttcg tctttttttt ttttttcgtc tttttttttt ttttcgtctt      60
tttttttttt ttcgtctttt tttttttttt cgtctttttt tttttttcg tctttttttt     120 ttttttcgtc tttttttttt ttttcgtctt tttttttttt ttcgtctttt tttttttttt     180
cgtctttttt tttttttcg tctttttttt ttttttcgtc tttttttttt ttttcgtctt     240
tttttttttt ttcgtctttt tttttttttt cgtctttttt tttttttcg tctttttttt     300 ttttttcgtc tttttttttt ttttcgtctt ttttggggg gggg                      344
```